United States Patent

Bernardi et al.

[11] 4,382,940
[45] May 10, 1983

[54] ERCOLINE DERIVATIVES AND THERAPEUTIC COMPOSITIONS HAVING CNS AFFECTING ACTIVITY

[75] Inventors: Luigi Bernardi; Germano Bosisio; Sergio Mantegani; Alessandro Rossi; Aldemio Temperilli, all of Milan, Italy

[73] Assignee: Farmitalia Carlo Erba S.p.A., Italy

[21] Appl. No.: 211,920

[22] Filed: Dec. 1, 1980

[30] Foreign Application Priority Data

Dec. 6, 1979 [GB] United Kingdom ............... 7942079
Mar. 1, 1980 [GB] United Kingdom ............... 8007029
May 29, 1980 [GB] United Kingdom ............... 8017518

[51] Int. Cl.³ .................. C07D 457/02; A61K 31/55
[52] U.S. Cl. ..................................... 424/261; 546/67
[58] Field of Search ................ 546/67; 544/361, 346; 424/261

[56] References Cited

U.S. PATENT DOCUMENTS 3,228,943  1/1966  Bernardi et al. ............... 544/361
3,646,046  2/1972  Arcamone et al. ............. 260/285.5
3,959,288  5/1976  Bach et al. ..................... 546/67
4,075,212  2/1978  Bach et al. ..................... 546/67
4,197,299  4/1980  Ferrari et al. .................. 546/67

FOREIGN PATENT DOCUMENTS 4664   10/1979  European Pat. Off. .......... 424/261
959261  5/1964  United Kingdom ............. 546/67
981827  1/1965  United Kingdom ............. 546/67

OTHER PUBLICATIONS

Bernardi et al., "Ergoline Derivatives" Il Farmaco, (Sci. Ed.) pp. 789-801 (789).
Beran et al., 6-Substituted Derivatives of D-8.

Primary Examiner—Donald G. Daus
Assistant Examiner—G. Hendricks
Attorney, Agent, or Firm—Stevens, Davis, Miller & Mosher

[57] ABSTRACT

Compounds are disclosed of formula (I)

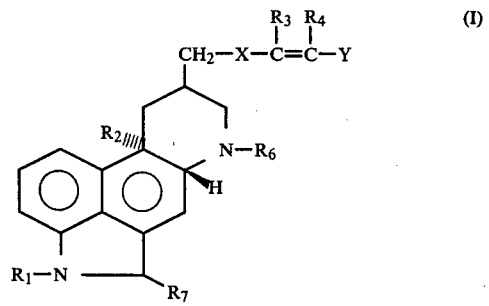

wherein $R_1$ represents a hydrogen atom or a methyl group;
$R_2$ represents a hydrogen atom or a methoxy group;
X represents an oxygen or sulphur atom or an NH or $NCH_3$ group;
$R_3$ represents a hydrogen atom, a trifluoromethyl or phenyl group or a hydrocarbon group having from 1 to 4 carbon atoms;
$R_4$ represents a hydrogen atom, a methyl or acetyl group or a hydrocarbon having from 1 to 4 carbon atoms, or $R_3$ and $R_4$ together represent a 3- or 4-membered carbon atom chain;
Y represents an electron-withdrawing group such as a cyano, nitro, alkylsulphonyl or alkylsulprinyl group or a group of the formula $COR_5$ wherein $R_5$ represents an alkyl group having from 1 to 4 carbon atoms or a phenyl, alkoxy, amino or N-substituted amino group or $R_5$ and $R_3$ together represent a 2- or 3-membered carbon atom chain;
$R_6$ represents a hydrocarbon group having from 1 to 4 carbon atoms or a benzyl or phenethyl group; and
$R_7$ represents a hydrogen or halogen atom or a methyl or formyl group or a group of the formula $SR_8$ wherein $R_8$ represents a hydrocarbon group having from 1 to 4 carbon atoms or a phenyl group;

and the pharmaceutically acceptable addition salts with organic or inorganic acids thereof. A process for producing these compounds is also disclosed.

These compounds are useful antidepressant, anxiolytic and neuroleptic agents. They also display from moderate to good antiprolactinic and antihypertensive activity.

48 Claims, No Drawings

ERCOLINE DERIVATIVES AND THERAPEUTIC COMPOSITIONS HAVING CNS AFFECTING ACTIVITY

The invention relates to ergot derivatives, a process for preparing same, and therapeutic compositions containing them.

The ergoline derivatives according to this invention are of the general formula (I):

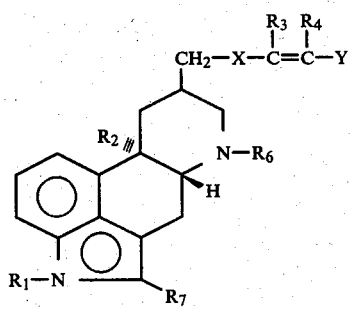

wherein $R_1$ represents a hydrogen atom or a methyl group;

$R_2$ represents a hydrogen atom or a methoxy group;

X represents an oxygen or sulphur atom or an NH or $NCH_3$ group;

$R_3$ represents a hydrogen atom, a trifluoromethyl or phenyl group or a hydrocarbon group having from 1 to 4 carbon atoms;

$R_4$ represents a hydrogen atom, a methyl or acetyl group or a hydrocarbon group having from 1 to 4 carbon atoms, or $R_3$ and $R_4$ together represent a 3- or 4-membered carbon atom chain;

Y represents an electron-withdrawing group such as a cyano, nitro, alkylsulphonyl or alkylsulphinyl group or a group of the formula $COR_5$ wherein $R_5$ represents an alkyl group having from 1 to 4 carbon atoms or a phenyl, alkoxy, amino or N-substituted amino group, or $R_5$ and $R_3$ together represent a 2- or 3-membered carbon atom chain;

$R_6$ represents a hydrocarbon group having from 1 to 4 carbon atoms or a benzyl or phenethyl group; and $R_7$ represents a hydrogen or halogen atom or a methyl or formyl group or a group of the formula $SR_8$ wherein $R_8$ represents a hydrocarbon group having from 1 to 4 carbon atoms or a phenyl group;

and the pharmaceutically acceptable addition salts thereof with organic or inorganic acids.

In the general formula (I) the term "halogen" should be construed as preferably encompassing chlorine and bromine atoms; nevertheless, the term "halogen" also encompasses the fluorine atom.

In the definitions above of $R_3$, $R_4$, $R_6$ and $R_8$ referring to a hydrocarbon group having from 1 to 4 carbon atoms, this is intended to include alkyl, cycloalkyl and unsaturated (both ethylenically and acetylenically) groups.

Representative moieties include methyl, ethyl, n-propyl, isopropyl, butyl, t-butyl, isobutyl, cyclopropyl, methylcyclopropyl, vinyl, allyl and propargyl.

Ergoline derivatives of the general formula (I) as above defined may be prepared by condensing a compound of the general formula (II) below with an alkaline salt of the formula (III) below, in hexamethylphosphotriamide as solvent.

In the general formula (II) and (III), $R_1$, $R_2$, $R_3$, $R_4$, $R_6$, $R_7$, X and Y have the meanings given above, and M represents an alkali metal.

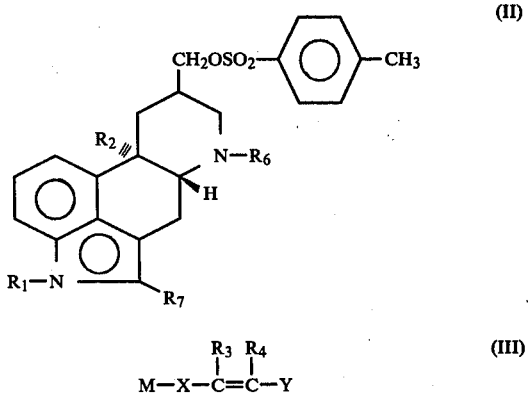

$$M-X-\overset{R_3}{\underset{|}{C}}=\overset{R_4}{\underset{|}{C}}-Y \quad (III)$$

The compounds of formula (III) are well-known compounds.

The compounds of formula (II) are well-known in the art or can be made from precursor compounds by well-known reactions. See, for example, J. Krepelka et al., "Collection Czechoslov. Chem. Comm.", 42, 1209–1212 (1977), and L. Bernardi et al., "Il Farmaco-Ed Sci.", 789–795 (1975).

In our co-pending U.S. application Ser. No. 72,289, filed Sept. 4, 1979, reaction between compounds of formula (II) and formula (III) was described. This reaction was carried out in the presence of polar aprotic solvents, such as dimethylsulphoxide. C-alkylation derivatives were the products of such a condensation.

Now we have surprisingly found (in accordance with the present invention) that the products of X-alkylation, wherein X has the meaning ascribed to it above, are obtained almost exclusively when hexamethylphosphotriamide is used as solvent.

The condensation, which is a process within the scope of this invention, may be carried out at a temperature in the range from 50° to 100° C.; the reaction is usually terminated after 2 to 10 hours.

The condensation products may be purified by conventional procedures. Chromatography over silicagel is especially suitable.

Formation of the desired pharmaceutically-acceptable addition salts with organic and inorganic acids is carried out by per se known methods; e.g. by reaction with an appropriate acid.

The compounds according to this invention (including the pharmaceutically-acceptable salts thereof) are useful antidepressant, anxiolitic and neuroleptic agents and they also display from moderate to good antiprolactinic and antihypertensive activity.

The profiles of the central sedative pharmacological activity were obtained by Irwin's observational assessment of mouse behavior (Irwin S.-Psychopharmacologia, Berl. 13, 222, 1968), which also gives an indication of the orientative acute toxicity after 7 days observation, and by antagonism to the central amphetamine-induced hypothermia.

The results obtained with compounds according to the present invention are reported below in Table 1.

TABLE 1

| Compounds | Amphetamine antagonism (ED$_{50}$, mg/kg p.o.) | Orientative acute toxicity (LD$_{50}$, mg/kg p.o.) |
|---|---|---|
| 355/1171 (Ex. 1) | 0.023 | >800 |
| 355/1240 (Ex. 12) | 1.8 | 200 |
| 355/1295 (Ex. 42) | 1.8 | >400 |
| 355/1357 (Ex. 27) | 2.5 | >300 |
| 355/1363 (Ex. 31) | 2.4 | 400 |

For measuring the antagonism to the central amphetamine-induced hypothermia (Janssen P. A. J., Niemegeers C. J. E., Schellekens K. H. L. and Lenaerts I. M., Arzeimittel-Forsch. 17, (7), 841, 1967) the compounds were orally administered to male mice, in a dose range between 0.01 and 10 mg/kg, 30 minutes before the intraperitoneal injection of 10 mg/kg of d-amphetamine sulphate. The antagonism to hypothermia was evaluated 60 minutes after amphetamine administration.

The title compounds proved to be active potential antidepressant agents as predicted by their antagonism to reserpine-induced blepharospasm and hypothermia.

The tests were performed in an air-conditioned room at the constant temperature of 19°±1° C. Randomized groups of male mice were respectively treated by gavage with appropriate screening doses (from a maximum of 25 mg/kg below) of the test compounds, suspended in the vehicle (Methocel 0.5%; 1 ml/100 g b.w.), or with the vehicle alone.

One hour later the animals received an i.p. injection of reserpine (1.5 mg/kg; 1 ml/100 g b.w.), and one of the control groups the same volume of the vehicle alone (blank controls). Three hours after pretreatments, i.e. two hours after reserpine or vehicle treatments, blepharospasm was evaluated in scores as proposed by RUBIN et al. (J. Pharmacol., 120:125, 1957).

Two hours after the above-mentioned evaluation the rectal temperature of the animals was recorded by an appropriate probe connected to a digital thermometer (ELLAB DU-3).

As reported in Table 2 below, the title compounds proved to be strongly active in preventing the considered reserpine-induced symptoms with ED$_{50}$'s falling in a dose range of from 0.1 to 10 mg/kg p.o. and with very low orientative acute toxicities. The tricyclic antidepressant imipramine, used as the reference standard drug, prevented reserpine-induced blepharospasm and hypothermia with ED$_{50}$'s respectively of 3.1 and 18.2 mg/kg p.o. and showed quite higher orientative acute toxicity in mice.

TABLE 2

| Compounds | Reserpine antagonism (ED$_{50}$, mg/kg p.o.) | | Orientative acute toxicity (LD$_{50}$, mg/kg p.o.) |
|---|---|---|---|
| | Blepharospasm | hypothermia | |
| 355/1228 (Ex. 3) | 0.14 | 0.39 | >600 |
| 355/1206 (Ex. 41) | 3.1 | 7.7 | >800 |
| 355/1301 (Ex. 19) | 0.46 | 0.57 | 300 |
| 355/1311 (Ex. 16) | 1.5 | 3.4 | 300 |
| 355/1335 (Ex. 29) | 0.2 | 0.3 | 200 |

The following examples are given in order still further to illustrate the invention.

EXAMPLE 1

6-Methyl-3-[(3-buten-2-one-4-methyl)-4-oxymethyl]-ergoline ($R_6$=CH$_3$; X=O; $R_3$=CH$_3$; Y=COCH$_3$; $R_4$=H; $R_2$=H; $R_7$=H; $R_1$=H)

A mixture of 4.1 g of 6-methyl-8β-tosyloxymethylergoline and 2.44 g of acetylacetone sodium salt in 30 ml of hexamethylphosphotriamide was heated to 80° C. and maintained at that temperature for 3 hours. The resulting solution was poured into 500 ml of water and the precipitate was filtered off and purified by crystallization from acetone to give 2.3 g of the title compound, m.p. 247°-249° C.

EXAMPLE 2

6-Methyl-8-[(2-cyclohexenon)-3-oxymethyl]-ergoline ($R_2$, $R_7$, $R_1$, $R_4$=H; $R_6$=CH$_3$; X=O; Y and $R_3$=CO—CH$_2$—CH$_2$—CH$_2$—)

Operating as in Example 1, but employing 1,3-cyclohexandione sodium salt in place of acetylacetone sodium salt, the title compound, m.p. 224°-226° C., was obtained in 65% yield.

EXAMPLE 3

6-Methyl-8-[(2-cyclopentenon)-3-oxymethyl]-ergoline ($R_2$, $R_7$, $R_1$, $R_4$=H; $R_6$=CH$_3$; X=O; Y and $R_3$=CO—CH$_2$—CH$_2$—)

Operating as in Example 1, but employing 1,3-cyclopentandione sodium salt in place of acetylacetone sodium salt, the title compound, m.p. 215°-217° C., was obtained in 70% yield.

EXAMPLE 4

6-Methyl-8-[(1-phenyl-3-methyl-2-propen-1-one)-3-oxymethyl]-ergoline ($R_2$, $R_7$, $R_1$, $R_4$=H; $R_6$=CH$_3$; $R_3$=CH$_3$; X=O; Y=—CO-phenyl)

Operating as in Example 1, but employing benzoylacetone sodium salt in place of acetylacetone sodium salt, the title compound, m.p. 195°-197° C., was obtained in 75% yield.

EXAMPLE 5

6-Methyl-8-[(3-buten-2-one)-4-oxymethyl]-ergoline ($R_2$, $R_7$, $R_1$, $R_3$, $R_4$=H; Y=COCH$_3$; Y=O; $R_6$=CH$_3$)

Operating as in Example 1, but employing formylacetone sodium salt in place of acetylacetone sodium salt, the title compound, m.p. 156°-159° C., was obtained in 55% yield.

EXAMPLE 6

6-Methyl-8-[(1-acetyl-1-cyclohexen)-2-oxymethyl]-ergoline ($R_2$, $R_7$, $R_1$=H; $R_6$=$CH_3$; X=O; Y=$COCH_3$; $R_3$ and $R_4$=—$CH_2$—$CH_2$—$CH_2$—$CH_2$—)

Operating as in Example 1, but employing 2-acetyl-cyclohexanone sodium salt in place of acetylacetone sodium salt, the title compound, m.p. 147°-150° C., was obtained in 65% yield.

EXAMPLE 7

6-Methyl-8-[(1,3-diphenyl-2-propen-1-one)-3-oxymethyl]-ergoline ($R_1$, $R_7$, $R_2$, $R_4$=H; $R_6$=$CH_3$; X=O; Y=COphenyl; $R_3$=phenyl)

Operating as in Example 1, but employing dibenzoylmethane sodium salt in place of acetylacetone sodium salt, the title compound, m.p. 182°-184° C., was obtained in 75% yield.

EXAMPLE 8

6-Methyl-8-[(3-methylacrylic acid ethyl ester)-3-oxymethyl]-ergoline ($R_1$, $R_7$, $R_2$, $R_4$=H; $R_6$ and $R_3$=$CH_3$; X=O; Y=$COOC_2H_5$)

Operating as in Example 1, but employing ethyl acetoacetate sodium salt in place of acetylacetone sodium salt, the title compound, m.p. 215°-217° C., was obtained in 50% yield.

EXAMPLE 9

1,6-Dimethyl-8-[(3-buten-2-one-4-methyl)-4-oxymethyl]-ergoline ($R_1$, $R_6$, $R_3$=$CH_3$; $R_2$, $R_4$, $R_7$=H; X=O; Y=$COCH_3$)

Operating as in Example 1, but employing 1,6-dimethyl-8β-tosyloxymethylergoline in place of 6-methyl-8β-tosyloxymethylergoline, the title compound, m.p. 161°-163° C., was obtained in 70% yield.

EXAMPLE 10

1-6-Dimethyl-8-[(2-cyclopentenon)-3-oxymethyl]-ergoline ($R_2$, $R_4$, $R_7$,=H; $R_1$, $R_6$=$CH_3$; X=O; Y and $R_3$=—CO—$CH_2$—$CH_2$—)

Operating as in Example 3, but employing 1,6-dimethyl-8β-tosyloxymethylergoline in place of 6-methyl-8β-tosyloxymethylergoline, the title compound, m.p. 139°-141° C., was obtained in 80% yield.

EXAMPLE 11

1,6-Dimethyl-8-[(3-buten-2-one-4-methyl)-4-oxymethyl]-10-methoxyergoline ($R_1$, $R_6$, $R_3$=$CH_3$; $R_2$=$OCH_3$; $R_4$, $R_7$=H; X=O; Y=$COCH_3$)

Operating as in Example 1, but employing 1,6-dimethyl-8β-tosyloxymethyl-10-methoxyergoline in place of 6-methyl-8β-tosyloxymethylergoline, the title compound, m.p. 147°-149° C., was obtained in 60% yield.

EXAMPLE 12

1,6-Dimethyl-8-[(2-cyclopentenon)-3-oxymethyl]-10-methoxyergoline ($R_4$, $R_7$=H; $R_2$=$OCH_3$; $R_1$, $R_6$=$CH_3$; X=O; Y and $R_3$=—$COCH_2CH_2$—)

Operating as in Example 3, but employing 1,6-dimethyl-8β-tosyloxymethyl-10-methoxyergoline in place of 6-methyl-8β-tosyloxymethylergoline, the title compound, m.p. 158°-160° C., was obtained in 45% yield.

EXAMPLE 13

6-Methyl-8-[(3-buten-2-one-4-methyl)-4-oxymethyl]-10-methoxyergoline ($R_1$, $R_4$, $R_7$=H; $R_2$=$OCH_3$; $R_6$=$CH_3$; $R_3$=$CH_3$; X=O; Y=$COCH_3$)

Operating as in Example 1, but employing 6-methyl-8β-tosyloxymethyl-10-methoxyergoline in place of 6-methyl-8β-tosyloxymethylergoline, the title compound, m.p. 178°-180° C., was obtained in 55% yield.

EXAMPLE 14

6-Methyl-8-[(2-cyclopentenon)-3-oxymethyl]-10-methoxyergoline ($R_1$, $R_4$, $R_7$,=H; $R_6$=$CH_3$; $R_2$=$OCH_3$; X=O; Y and $R_3$=—CO—$CH_2CH_2$—)

Operating as in Example 3, but employing 6-methyl-8β-tosyloxymethyl-10-methoxyergoline in place of 6-methyl-8β-tosyloxymethylergoline, the title compound, m.p. 239°-241° C., was obtained in 63% yield.

EXAMPLE 15

1,6-Dimethyl-8-[(3-buten-2-one)-4-oxymethyl]ergoline ($R_2$, $R_3$, $R_4$, $R_7$=H; $R_1$, $R_6$=$CH_3$; Y=$COCH_3$; X=O)

Operating as in Example 5, but employing 1,6-dimethyl-8β-tosyloxymethylergoline in place of 6-methyl-8β-tosyloxymethylergoline, the title compound, m.p. 120°-122° C., was obtained in 45% yield.

EXAMPLE 16

6-Methyl-8-[(3-methylacrylic nitrile)-3-oxymethyl]-ergoline ($R_1$, $R_2$, $R_4$, $R_7$=H; $R_3$, $R_6$=$CH_3$; X=O; Y=CN)

Operating as in Example 1, but employing cyanoacetone sodium salt in place of acetylacetone sodium salt, the title compound, m.p. 210°-212° C., was obtained in 60% yield.

EXAMPLE 17

1,6-Dimethyl-8-[(3-methylacrylic nitrile)-3-oxymethyl]-ergoline ($R_2$, $R_4$, $R_7$,=H; $R_1$, $R_3$, $R_6$=$CH_3$; X=O; Y=CN)

Operating as in Example 16, but employing 1,6-dimethyl-8β-tosyloxymethylergoline in place of 6-methyl-8β-tosyloxymethylergoline, the title compound, m.p. 162°-164° C., was obtained in 70% yield.

EXAMPLE 18

2,6-Dimethyl-8-[(3-buten-2-one-4-methyl)-4-oxymethyl]-ergoline ($R_1$, $R_2$, $R_4$=H; $R_3$, $R_6$, $R_7$=CH$_3$; Y=COCH$_3$; X=O)

A mixture of 3.18 g of 2,6-dimethyl-8β-tosyloxymethylergoline and 1.65 g of acetylacetone sodium salt in 30 ml of hexamethylphosphotriamide was heated to 80° C. and maintained at that temperature for 3 hours. The resulting solution was poured into 500 ml of water and the precipitate was filtered off and purified by crystallization from ethanol to give 1.3 g of the title compound, m.p. 224°–225° C.

EXAMPLE 19

2,6-Dimethyl-8-[(2-cyclopentenon)-3-oxymethyl]-ergoline ($R_2$, $R_1$, $R_4$ = H; $R_6$, $R_7$ = CH$_3$;

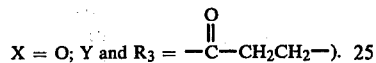

X = O; Y and $R_3$ = —C—CH$_2$CH$_2$—).

Operating as in Example 18, but employing 1,3-cyclopentadione sodium salt, in place of acetylacetone sodium salt, the title compound, m.p. 221°–223° C., was obtained in 60% yield.

EXAMPLE 20

6-Propyl-3-[(3-buten-2-one-4-methyl)-4-oxymethyl]-ergoline ($R_1$, $R_2$, $R_4$, $R_7$=H; $R_3$=CH$_3$; $R_6$=CH$_2$CH$_2$CH$_3$; Y=COCH$_3$; X=O)

Operating as in Example 18, but employing 6-propyl-8β-tosyloxymethylergoline in place of 2,6-dimethyl-8β-tosyloxymethylergoline, the title compound was obtained in 75% yield, m.p. 198°–201° C.

EXAMPLE 21

6-Propyl-8-[(2-cyclopentenon)-3-oxymethyl]-ergoline ($R_1$, $R_2$, $R_4$, $R_7$ = H; $R_6$ = CH$_2$CH$_2$CH$_3$;

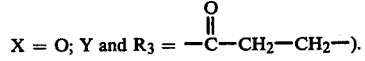

X = O; Y and $R_3$ = —C—CH$_2$—CH$_2$—).

Operating as in Example 20, but employing 1,3-cyclopentandione sodium salt in place of acetylacetone sodium salt, the title compound was obtained in 70% yield; m.p. 180°–183° C.

EXAMPLE 22

2-Bromo-6-methyl-8-[(3-buten-2-one-4-methyl)-4-oxymethyl]-ergoline ($R_1$, $R_2$, $R_4$=H; $R_3$=CH$_3$; $R_6$=CH$_3$; $R_7$=Br; Y=COCH$_3$; X=O)

Operating as in Example 18, but employing 2-bromo-6-methyl-8β-tosyloxymethylergoline in place of 2,6-dimethyl-8β-tosyloxymethylergoline, the title compound was obtained in 68% yield; m.p. 250°–251° C.

EXAMPLE 23

2-Chloro-6-methyl-8-[(3-buten-2-one-4-methyl)-4-oxymethyl]-ergoline ($R_1$, $R_2$, $R_4$=H; $R_3$, $R_6$=CH$_3$; $R_7$=Cl; Y=COCH$_3$; X=O)

Operating as in Example 18, but employing 2-chloro-6-methyl-8β-tosyloxymethylergoline, the title compound, m.p. 257°–260° C., was obtained in 70% yield.

EXAMPLE 24

2-Thiomethyl-6-methyl-8-[(3-buten-2-one-4-methyl)-4-oxymethyl]-ergoline ($R_1$, $R_2$, $R_4$=H; $R_3$, $R_6$=CH$_3$; $R_7$=SCH$_3$; Y=COCH$_3$; X=O)

Operating as described in Example 18, but employing 2-thiomethyl-8β-tosyloxymethylergoline, the title compound, m.p. 196°–198° C., was obtained in 65% yield.

EXAMPLE 25

2-Bromo-6--methyl-8-[(3-buten-2-one)-4-oxymethyl]-ergoline ($R_1$, $R_2$, $R_3$, $R_4$=H; $R_6$=CH$_3$; $R_7$=Br; Y=COCH$_3$; X=O)

Operating as in Example 22, but employing formylacetone sodium salt, the title compound, m.p. 108°–110° C., was obtained in 55% yield.

EXAMPLE 26

2-Chloro-6-methyl-8-[(3-buten-2-one)-4-oxymethyl]-ergoline ($R_1$, $R_2$, $R_3$, $R_4$=H; $R_6$=CH$_3$; $R_7$=Cl; Y=COCH$_3$; X=O)

Operating as in Example 23, but employing formylacetone sodium salt, the title compound, m.p. 117°–120° C., was obtained in 60% yield.

EXAMPLE B 27

2-Thiomethyl-6-methyl-8-[(3-buten-2-one)-4-oxymethyl]-ergoline ($R_1$, $R_2$, $R_3$, $R_4$=H; $R_6$=CH$_3$; $R_7$=SCH$_3$; Y=COCH$_3$; X=O)

Operating as in Example 24, but employing formylacetone sodium salt, the title compound, m.p. 162°–165°, was obtained in 70% yield.

EXAMPLE 28

2-Bromo-6-methyl-8-[(2-cyclopentenon)-3-oxymethyl]-ergoline $R_1$, $R_2$, $R_4$=H; $R_6$=CH$_3$; $R_7$=Br; Y and $R_3$=COCH$_2$CH$_2$—; X=O)

Operating as in Example 22, but employing 1,3-cyclopentandione sodium salt, the title compound, m.p. 216°–218° C., was obtained in 73% yield.

EXAMPLE 29

2-Chloro-6-methyl-8-[(2-cyclopentenon)-3-oxymethyl]-ergoline ($R_1$, $R_2$, $R_4$=H; $R_6$=$CH_3$; $R_7$=Cl; Y and $R_3$=—$COCH_2CH_2$; X=O)

Operating as in Example 23, but employing 1,3-cycopentadione sodium salt, the title compound, m.p. 230°–232° C., was obtained in 65% yield.

EXAMPLE 30

2-Thiomethyl-6-methyl-8-[(2-cyclopentenon)-3-oxymethyl]-ergoline ($R_1$, $R_2$, $R_4$=H; $R_6$=$CH_3$; $R_7$=$SCH_3$; Y and $R_3$=—$COCH_2$—$CH_2$—; X=O)

Operating as in Example 24, but employing 1,3-cyclopentandione sodium salt, the title compound, m.p 203°–205° C., was obtained in 64% yield.

EXAMPLE 31

6-Propyl-8-[(3-buten-2-one)-4-oxymethyl]-ergoline ($R_1$, $R_2$, $R_3$, $R_4$, $R_7$=H; $R_6$=$CH_2CH_2CH_3$; Y=$COCH_3$; X=O)

Operating as in Example 20, but employing formylacetone sodium salt, the title compound, m.p. 122°–124° C., was obtained in 55% yield.

EXAMPLE 32

6-Allyl-8-[(3-buten-2-one-4-methyl)-4-oxymethyl]-ergoline ($R_1$, $R_2$, $R_4$, $R_7$=H; $R_3$=$CH_3$; $R_6$=—$CH_2$—CH=$CH_2$; Y=$COCH_3$; X=O)

Operating as in Example 18, but employing 6-allyl-8β-tosyloxymethylergoline, the title compound, m.p. 195°–199° C., was obtained in 60% yield.

EXAMPLE 33

6-Allyl-8-[(2-cyclopentenon)-3-oxymethyl]-ergoline ($R_1$, $R_2$, $R_4$, $R_7$=H; $R_6$=—$CH_2$—CH=$CH_2$; X=O; Y and $R_3$=$COCH_2CH_2$—)

Operating as in Example 32, but employing 1,3-cyclopentandione sodium salt, the title compound, m.p. 198°–200° C., was obtained in 70% yield.

EXAMPLE 34

6-Allyl-8-[(3-buten-2-one)-4-oxymethyl]-ergoline ($R_1$, $R_2$, $R_3$, $R_4$, $R_7$=H; Y=$COCH_3$; X=O; $R_6$=—$CH_2CH$=$CH_2$)

Operating as in Example 32, but employing formylacetone sodium salt, the title compound, m.p. 118°–120° C., was obtained in 50% yield.

EXAMPLE 35

6-Isopropyl-8-[(3-buten-2-one-4-methyl)-4-oxymethyl]-ergoline ($R_1$, $R_2$, $R_4$, $R_7$=H; $R_3$=$CH_3$; $R_6$=$CH(CH_3)_2$; Y=$COCH_3$; X=O)

Operating as in Example 18, but employing 6-isopropyl-8β-tosyloxymethylergoline, the title compound, m.p. 213°–215° C., was obtained in 73% yield.

EXAMPLE 36

6-Isopropyl-8-[(2-cyclopentenon)-3-oxymethyl]-ergoline ($R_1$, $R_2$, $R_4$, $R_7$=H; $R_6$=$CH(CH_3)_2$; Y and $R_3$=$COCH_2CH_2$—; X=O)

Operating as in Example 35, but employing 1,3-cyclopentandione sodium salt, the title compound, m.p. 129°–132° C., was obtained in 65% yield.

EXAMPLE 37

6-Isopropyl-8-[(3-buten-2-one)-4-oxymethyl]-ergoline ($R_1$, $R_2$, $R_3$, $R_4$, $R_7$=H; $R_6$=$CH(CH_3)_2$; Y=$COCH_3$; X=O)

Operating as in Example 35, but employing formylacetone sodium salt, the title compound, m.p. 145°–148° C., was obtained in 55% yield.

EXAMPLE 38

6-Methyl-8-[(3-methylacrylic acid ethyl ester)-3-aminomethyl]-ergoline ($R_1$, $R_2$, $R_4$, $R_7$=H; $R_3$, $R_6$=$CH_3$; Y=$COOC_2H_5$; X=NH)

A mixture of 2 g of 6-methyl-8β-tosyloxymethyl-ergoline and 1 g of β-aminocrotonic acid ethyl ester sodium salt in 20 ml of hexamethylphosphotriamide was heated to 80° C. for a period of 7 hours. The reaction mixture was poured into iced water and the precipitate was filtered off and purified by crystallization from methanol to give 1.2 g of the title compound, m.p. 160°–162° C.

EXAMPLE 39

1,6-Dimethyl-8-[(3-methylacrylic acid ethyl ester)-3-aminomethyl]-ergoline ($R_1$, $R_3$, $R_6$=$CH_3$; $R_2$, $R_4$, $R_7$=H; Y=$COOC_2H_5$; X=NH)

Operating as in Example 38, but employing 1,6-dimethyl-8β-tosyloxymethyl-ergoline in place of 6-methyl-8β-tosyloxymethylergoline, the title compound, m.p. 143°–145° C., was obtained in 55% yield.

EXAMPLE 40

6-Methyl-8-[(3-buten-2-one-4-methyl)-4-aminomethyl]-ergoline ($R_1$, $R_2$, $R_4$, $R_7$=H; $R_3$ and $R_6$=$CH_3$; Y=$COCH_3$; X=NH)

Operating as in Example 38, but employing 4-amino-3-penten-2-one sodium salt in place of β-aminocrotonic acid ethyl ester sodium salt, the title compound, m.p. 193°–195° C., was obtained in 60% yield.

EXAMPLE 41

6-Methyl-8-[(2-cyclopentenon)-3-aminomethyl]-ergoline ($R_1$, $R_2$, $R_4$, $R_7$ = H; $R_6$ = $CH_3$;

Y and $R_3$ = $-\overset{\overset{\text{O}}{\|}}{C}CH_2CH_2-$; X = NH).

Operating as in Example 38, but employing 3-amino-2-cyclopenten-1-one sodium salt in place of β-aminocrotonic acid ethyl ester sodium salt, the title compound, m.p. 245°–247° C., was obtained in 45% yield.

EXAMPLE 42

1,6-Dimethyl-8-[(2-cyclopentenon)-3-aminomethyl]-ergoline ($R_1$, $R_6$=$CH_3$; $R_2$, $R_4$, $R_7$=H; Y and $R_3$=—CO—$CH_2$—$CH_2$; X=NH)

Operating as in Example 41, but employing 1,6-dimethyl-8β-tosyloxymethylergoline in place of 6-methyl-8β-tosyloxymethylergoline, the title compound, m.p. 124°–126° C., was obtained in 50% yield.

EXAMPLE 43

6-Methyl-8-[(1,3-diphenyl-2-propen-1-one)-3-aminomethyl]-ergoline ($R_1$, $R_2$, $R_4$, $R_7$=H; $R_6$=$CH_3$; $R_3$=phenyl; Y=COphenyl; X=NH)

Operating as in Example 38, but employing 3-amino-1,3-diphenyl-2-propen-1-one sodium salt, the title compound, m.p. 145°–147° C., was obtained in 45% yield.

EXAMPLE 44

6-Methyl-8-[(2-cyclohexenon)-3-aminomethyl]-ergoline ($R_1$, $R_2$, $R_4$, $R_7$=H; $R_6$=$CH_3$; Y and $R_3$=—COCH$_2$CH$_2$CH$_2$—; X=NH)

Operating as in Example 38, but employing 3-amino-2-cyclohexen-1-one sodium salt, the title compound, m.p. 280°–282° C., was obtained in 65% yield.

EXAMPLE 45

6-Methyl-8-[(1-acetyl-1-cyclohexen)-2-aminomethyl]-ergoline ($R_1$, $R_2$, $R_7$=H; $R_3$ and $R_4$=—CH$_2$CH$_2$CH$_2$CH$_2$—; $R_6$=$CH_3$; Y=COCH$_3$; X=NH)

Operating as in Example 38, but employing 2-amino-1-acetyl-1-cyclohexene sodium salt, the title compound, m.p. 212°–214° C., was obtained in 65% yield.

EXAMPLE 46

6-Methyl-8-[(1-phenyl-3-methyl-2-propen-1-one)-3-aminomethyl]-ergoline ($R_1$, $R_2$, $R_4$, $R_7$=H; Y=CO phenyl; $R_3$, $R_6$=$CH_3$; X=NH)

Operating as in Example 38, but employing 3-amino-1-phenyl-3-methyl-2-propen-1-one sodium salt, the title compound, m.p. 150°–153° C., was obtained in 70% yield.

Preferred embodiments of the generic invention are the title compounds referred to in the 46 examples above.

What is claimed is:

1. A compound of the formula:

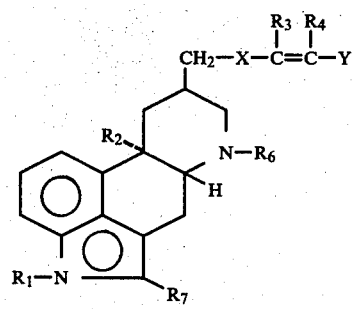

wherein $R_1$ is a hydrogen atom or methyl;
$R_2$ is a hydrogen atom or methoxy;
X is an oxygen atom or NH;
$R_3$ is a hydrogen atom, phenyl, or methyl;
$R_4$ is a hydrogen atom, or
$R_3$ and $R_4$ together represent a 4-membered saturated carbon atom chain;
Y is cyano or a group of the formula COR$_5$ wherein $R_5$ is methyl, phenyl, or ethoxy; or
$R_5$ and $R_3$ together represent a 2- or 3-membered saturated carbon atom chain;
$R_6$ is $C_1$-$C_3$ alkyl or allyl, and
$R_7$ is a hydrogen atom, a chlorine atom, a bromine atom, methyl, or SCH$_3$, and
a pharmaceutically acceptable acid addition salt thereof.

2. A compound as defined in claim 1 which is 6-Methyl-8-[(3-buten-2-one-4-methyl)-4-oxymethyl]-ergoline.

3. A compound as defined in claim 1 which is 6-Methyl-8-[(2-cyclohexenon)-3-oxymethyl]-ergoline.

4. A compound as defined in claim 1 which is 6-Methyl-8-[(2-cyclopentenon)-3-oxymethyl]-ergoline.

5. A compound as defined in claim 1 which is 6-Methyl-8-[(1-phenyl-3-methyl-2-propen-1-one)-3-oxymethyl]-ergoline.

6. A compound as defined in claim 1 which is 6-Methyl-8-[(3-buten-2-one)-4-oxymethyl]-ergoline.

7. A compound as defined in claim 1 which is 6-Methyl-8-[(1-acetyl-1-cyclohexen)-2-oxymethyl]-ergoline.

8. A compound as defined in claim 1 which is 6-Methyl-8-[(1,3-diphenyl-2-propen-1-one)-3-oxymethyl]-ergoline.

9. A compound as defined in claim 1 which is 6-Methyl-8-[(3-methylacrylic acid ethyl ester)-3-oxymethyl]-ergoline.

10. A compound as defined in claim 1 which is 1,6-Dimethyl-8-[(3-buten-2-one-4-methyl)-4-oxymethyl]-ergoline.

11. A compound as defined in claim 1 which is 1,6-Dimethyl-8-[(2-cyclopentenon)-3-oxymethyl]-ergoline.

12. A compound as defined in claim 1 which is 1,6-Dimethyl-8-[(3-buten-2-one-4-methyl)-4-oxymethyl]-10-methoxyergoline.

13. A compound as defined in claim 1 which is 1,6-Dimethyl-8-[(2-cyclopentenon)-3-oxymethyl]-10-methoxyergoline.

14. A compound as defined in claim 1 which is 6-Methyl-8-[(3-buten-2-one-4-methyl)-4-oxymethyl]-10-methoxyergoline.

15. A compound as defined in claim 1 which is 6-Methyl-8-[(2-cyclopentenon)-3-oxymethyl]-10-methoxyergoline.

16. A compound as defined in claim 1 which is 1,6-Dimethyl-8-[(3-buten-2-one)-4-oxymethyl]-ergoline.

17. A compound as defined in claim 1 which is 6-Methyl-8-[(3-methylacrylic nitrile)-3-oxymethyl]-ergoline.

18. A compound as defined in claim 1 which is 1,6-Dimethyl-8-[(3-methylacrylic nitrile)-3-oxymethyl]-ergoline.

19. A compound as defined in claim 1 which is 2,6-Dimethyl-8-[(3-buten-2-one-4-methyl)-4-oxymethyl]-ergoline.

20. A compound as defined in claim 1 which is 2,6-Dimethyl-8-[(2-cyclopentenon)-3-oxymethyl]-ergoline.

21. A compound as defined in claim 1 which is 6-Propyl-8-[(3-buten-2-one-4-methyl)-4-oxymethyl]-ergoline.

22. A compound as defined in claim 1 which is 6-Propyl-8-[(2-cyclopentenon)-3-oxymethyl]-ergoline.

23. A compound as defined in claim 1 which is 2-Bromo-6-methyl-8-[(3-buten-2-one-4-methyl)-4-oxymethyl]-ergoline.

24. A compound as defined in claim 1 which is 2-Chloro-6-methyl-8-[(3-buten-2-one-4-methyl)-4-oxymethyl]-ergoline.

25. A compound as defined in claim 1 which is 2-Thiomethyl-6-methyl-8-[(3-buten-2-one-4-methyl)-4-oxymethyl]-ergoline.

26. A compound as defined in claim 1 which is 2-Bromo-6-methyl-8-[(3-buten-2-one)-4-oxymethyl]-ergoline.

27. A compound as defined in claim 1 which is 2-Chloro-6-methyl-8-[(3-buten-2-one)-4-oxymethyl]-ergoline.

28. A compound as defined in claim 1 which is 2-Thiomethyl-6-methyl-8-[(3-buten-2-one)-4-oxymethyl]-ergoline.

29. A compound as defined in claim 1 which is 2-Bromo-6-methyl-8-[(2-cyclopentenon)-3-oxymethyl]-ergoline.

30. A compound as defined in claim 1 which is 2-Chloro-6-methyl-8-[(2-cyclopentenon)-3-oxymethyl]-ergoline.

31. A compound as defined in claim 1 which is 2-Thiomethyl-6-methyl-8-[(2-cyclopentenon)-3-oxymethyl]-ergoline.

32. A compound as defined in claim 1 which is 6-Propyl-8-[(3-buten-2-one)-4-oxymethyl]-ergoline.

33. A compound as defined in claim 1 which is 6-Allyl-8-[(3-buten-2-one-4-methyl)-4-oxymethyl]-ergoline.

34. A compound as defined in claim 1 which is 6-Allyl-8-[(2-cyclopentenon)-3-oxymethyl]-ergoline.

35. A compound as defined in claim 1 which is 6-Allyl-8-[(3-buten-2-one)-4-oxymethyl]-ergoline.

36. A compound as defined in claim 1 which is 6-Isopropyl-8-[(3-buten-2-one-4-methyl)-4-oxymethyl]-ergoline.

37. A compound as defined in claim 1 which is 6-Isopropyl-8-[(2-cyclopentenon)-3-oxymethyl]-ergoline.

38. A compound as defined in claim 1 which is 6-Isopropyl-8-[(3-buten-2-one)-4-oxymethyl]-ergoline.

39. A compound as defined in claim 1 which is 6-Methyl-8-[(3-methylacrylic acid ethyl ester)-3-aminomethyl]-ergoline.

40. A compound as defined in claim 1 which is 1,6-Dimethyl-8-[(3-methylacrylic acid ethyl ester)-3-aminomethyl]-ergoline.

41. A compound as defined in claim 1 which is a 6-Methyl-8-[(3-buten-2-one-4-methyl)-4-aminomethyl]-ergoline.

42. A compound as defined in claim 1 which is 6-Methyl-8-[(2-cyclopentenon)-3-aminomethyl]-ergoline.

43. A compound as defined in claim 1 which is 1,6-Dimethyl-8-[(2-cyclopentenon)-3-aminomethyl]-ergoline.

44. A compound as defined in claim 1 which is 6-Methyl-8-[(1,3-diphenyl-2-propen-1-one)-3-aminomethyl]-ergoline.

45. A compound as defined in claim 1 which is 6-Methyl-8-[(2-cyclohexenon)-3-aminomethyl]-ergoline.

46. A compound as defined in claim 1 which is 6-Methyl-8-[(1-acetyl-1-cyclohexen)-2-aminomethyl]-ergoline.

47. A compound as defined in claim 1 which is 6-Methyl-8-[(1-phenyl-3-methyl-2-propen-1-one)-3-aminomethyl]-ergoline.

48. A therapeutic composition containing a compound as defined in claim 1 as active ingredient, together with pharmaceutically-acceptable additives.

* * * * *

UNITED STATES PATENT AND TRADEMARK OFFICE
CERTIFICATE OF CORRECTION

PATENT NO. : 4,382,940
DATED : May 10, 1983
INVENTOR(S) : Luigi BERNARDI et al

It is certified that error appears in the above-identified patent and that said Letters Patent are hereby corrected as shown below:

[54] In the title:

change "ERCOLINE" to -- ERGOLINE --.

[57] In the Abstract, on the title page:

After the formula, line 14, change "alkylsulprinyl"

to -- alkylsulphinyl --.

Column 1, line 1, change "ERCOLINE" to -- ERGOLINE --.

Signed and Sealed this

Sixth Day of September 1983

[SEAL]

Attest:

GERALD J. MOSSINGHOFF

Attesting Officer      Commissioner of Patents and Trademarks